United States Patent [19]
Schmid et al.

[11] Patent Number: 5,962,475
[45] Date of Patent: Oct. 5, 1999

[54] SUBSTITUTED BENZO(B)THIOPHENE COMPOUNDS HAVING ACTIVITY AS SELECTIVE ESTROGEN RECEPTOR MODULATORS

[75] Inventors: Christopher Randall Schmid, Indianapolis; James Patrick Sluka, Greenwood, both of Ind.; Kristin Sue Marron, San Diego, Calif.

[73] Assignee: Eli Lilly and Company, Indianapolis, Ind.

[21] Appl. No.: 08/956,802

[22] Filed: Oct. 23, 1997

Related U.S. Application Data

[60] Provisional application No. 60/029,056, Oct. 25, 1996.
[51] Int. Cl.⁶ ...................... A61K 31/445; C07D 409/04; C07D 417/04; C07D 333/56
[52] U.S. Cl. .......................... 514/324; 514/442; 514/443; 514/146; 546/202; 548/525; 549/51
[58] Field of Search ........................... 546/202; 548/525; 549/51; 514/324, 442, 443, 146

[56] References Cited

U.S. PATENT DOCUMENTS

| | | | |
|---|---|---|---|
| 5,589,482 | 12/1996 | Thompson | 514/305 |
| 5,643,896 | 7/1997 | Cullinan | 514/146 |

FOREIGN PATENT DOCUMENTS

| | | |
|---|---|---|
| 0062503 | 4/1982 | European Pat. Off. . |
| 0641791A1 | 11/1992 | European Pat. Off. . |
| 0584952A1 | 7/1993 | European Pat. Off. . |
| 0617030A1 | 3/1994 | European Pat. Off. . |
| 0731098A1 | 3/1996 | European Pat. Off. . |
| 0738725A2 | 4/1996 | European Pat. Off. . |
| 95/10513 WO | 4/1995 | WIPO . |
| 9609040A1 WO | 9/1995 | WIPO . |
| 9609041A1 | 9/1995 | WIPO . |

OTHER PUBLICATIONS

Ruenitz, P.C. Drugs for Osteoporosis Prevention: Mechanisms of Bone Maintenance *Current Medicinal Chemistry 1995* 2.791–802 vol. 2, No. 4, pp.

Black, L.J.–Biological Actions and Binding Properties of a New Estrogen Antagonist, LY1107018 *Hormone Antagonists*,Editor M.K. Agarwal, pp. 129–145 (1982).

*Primary Examiner*—Cclia Chang
*Attorney, Agent, or Firm*—Gilbert T. Voy

[57] ABSTRACT

The present invention provides compounds with nitrogen, sulfur or carbon linked basic side chains of formula

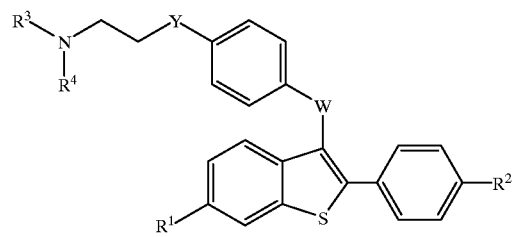

where $R^1$ and $R^2$ are independently hydrogen, halo, hydroxy, alkoxy, alkylcarbonyloxy, alkoxycarbonyl, alkoxycarbonyloxy, arylcarbonyloxy, aryloxycarbonyloxy, or alkylsulfonyloxy; O—$SO_2$—($C_4$–$C_6$ alkyl), chloro, fluoro, or bromo; W is CHOH, C(O), or $CH_2$; Y is —$CH_2$—, —NH—, —NMe—, —S—, —$SO_2$—; and $R^3$ and $R^4$ are independently hydrogen, alkyl, alkylcarbonyl, alkylaminocarbonyl, or arylcarbonyl, or together with the nitrogen to which they are attached form 1-pyrrolidinyl, 1-piperidinyl, or a 5- or 6-membered imide or cyclic amide ring.

The present invention also provides pharmaceutical compositions containing the compounds optionally containing estrogen or progestin, and the use of such compounds, alone, or in combination with estrogen or progestin, for treating osteoporosis, aortal smooth muscle cell proliferation, (particularly restenosis), and estrogen-dependent cancer (particularly breast cancer).

16 Claims, No Drawings

SUBSTITUTED BENZO(B)THIOPHENE COMPOUNDS HAVING ACTIVITY AS SELECTIVE ESTROGEN RECEPTOR MODULATORS

CROSS-REFERENCE TO RELATED APPLICATIONS

This application claims priority to provisional application Ser. No. 60/029,056 filed Oct. 25, 1996.

TECHNICAL FIELD

This invention relates to organic compounds having pharmacological activity, to compositions containing the compounds, to medical methods of treatment employing the compounds, and to chemical processes and intermediates for their production. More particularly, the present invention concerns a class of (substituted alkylaminophenyl)- and (substituted alkylthiophenyl)benzo[b]thiophene compounds, pharmaceutical formulations containing the compounds, their use in the treatment of conditions associated with post-menopausal syndrome, and estrogen dependent cancers, uterine fibroid disease, endometriosis, and aortal smooth muscle cell proliferation.

BACKGROUND OF THE INVENTION

"Post-menopausal syndrome" is a term used to describe various pathological conditions which frequently affect women who have entered into or completed the physiological metamorphosis known as menopause. Although numerous pathologies are contemplated by the use of this term, three major effects of post-menopausal syndrome are the source of the greatest long-term medical concern: osteoporosis, cardiovascular effects such as hyperlipidemia, and estrogen-dependent cancer, particularly breast and uterine cancer.

Osteoporosis describes a group of diseases which arise from diverse etiologies, but which are characterized by the net loss of bone mass per unit volume. The consequence of this loss of bone mass is the failure of the skeleton to provide adequate structural support for the body resulting in bone fractures.

One of the most common types of osteoporosis is that associated with menopause. Most women lose from about 20% to about 60% of the bone mass in the trabecular compartment of the bone within 3 to 6 years after the cessation of mensus. This rapid loss is generally associated with an increase of bone resorption and formation. However, the resorptive cycle is more dominant and the result is a net loss of bone mass. Osteoporosis is a common and serious disease among post-menopausal women.

There are an estimated 25 million women in the United States, alone, who are afflicted with this disease. The results of osteoporosis are personally harmful and also account for a large economic loss due to its chronicity and the need for extensive and long term support (hospitalization and nursing home care) from the disease sequelae. This is especially true in more elderly patients. Additionally, although osteoporosis is not generally thought of as a life threatening condition, a 20% to 30% mortality rate is related with hip fractures in elderly women. A large percentage of this mortality rate can be directly associated with post-menopausal osteoporosis.

The most vulnerable tissue in the bone to the effects of post-menopausal osteoporosis is the trabecular bone. This tissue is often referred to as spongy or cancellous bone and is particularly concentrated near the ends of the bone (near the joints) and in the vertebrae of the spine. The trabecular tissue is characterized by small osteoid structures which inter-connect with each other, as well as the more solid and dense cortical tissue which makes up the outer surface and central shaft of the bone. This inter-connected network of trabeculae gives lateral support to the outer cortical structure and is critical to the biomechanical strength of the overall structure.

In post-menopausal osteoporosis, it is primarily the net resorption and loss of the trabeculae which leads to the failure and fracture of bone. In light of the loss of the trabeculae in post-menopausal women, it is not surprising that the most common fractures are those associated with bones which are highly dependent on trabecular support, e.g., the vertebrae, the neck of the weight bearing bones such as the femur and the fore-arm. Indeed, hip fracture, collies fractures, and vertebral crush fractures are hallmarks of post-menopausal osteoporosis.

At this time, the only generally accepted method for treatment of post-menopausal syndrome is estrogen replacement therapy. Although therapy is generally successful, patient compliance with the therapy is low primarily because estrogen treatment frequently produces undesirable side effects.

Prior to menopause, most women have less incidence of cardiovascular disease than age-matched men. Following menopause, however, the rate of cardiovascular disease in women increases to match the rate seen in men. This increased risk has been linked to the loss of estrogen and, in particular, to the loss of estrogen's ability to regulate the levels of serum lipids. The nature of estrogen's ability to regulate serum lipids is not well understood, but evidence to date indicates that estrogen can upregulate the low density lipid (LDL) receptors in the liver to remove excess cholesterol. Additionally, estrogen appears to have some effect on the biosynthesis of cholesterol, and other beneficial effects on cardiovascular health.

It has been reported in the literature that post-menopausal women undergoing estrogen replacement therapy experience a return of serum lipid concentrations to those of the pre-menopausal state. Thus, estrogen would appear to be a reasonable treatment for this condition. However, the side-effects of estrogen replacement therapy are not acceptable to many women, thus limiting the use of this therapy. An ideal therapy for this condition would be an agent which would regulate the serum lipid levels as does estrogen, but would be devoid of the side-effects and risks associated with estrogen therapy.

The third major pathology associated with post-menopausal syndrome is estrogen-dependent breast cancer and, to a lesser extent, estrogen-dependent cancers of other organs, particularly the uterus. Although such neoplasms are not solely limited to a post-menopausal women, they are more prevalent in the older, post-menopausal population. Current chemotherapy of these cancers has relied heavily on the use of anti-estrogen compounds such as, for example, Tamoxifen. Although such mixed agonist-antagonists have beneficial effects in the treatment of these cancers, and the estrogenic side-effects are tolerable in acute life-threatening situations, they are not ideal. For example, these agents may have stimulatory effects on certain cancer cell populations in the uterus due to their estrogenic (agonist) properties and they may, therefore, be contraproductive in some cases. A better therapy for the treatment of these cancers would be an agent which is an anti-estrogen compound having negligible or no estrogen agonist properties on reproductive tissues.

In response to the clear need for new pharmaceutical agents which are capable of alleviating the symptoms of, inter alia, post-menopausal syndrome, the present invention provides new compounds, pharmaceutical compositions thereof, and methods of using such compounds for the treatment of post-menopausal syndrome and other estrogen-related pathological conditions such as those mentioned below. The reduction of bone density and mass leading to osteoporosis that more rarely occurs in men is also tied to the loss of hormonal regulation and is, therefore, also a target for therapy according to the compounds and methods of the current invention.

Uterine fibrosis is an old and ever present clinical problem known by a variety of names, including uterine hypertrophy, uterine lieomyomata, myometrial hypertrophy, fibrosis uteri, and fibrotic metritis. Essentially, uterine fibrosis is a condition where there is an inappropriate deposition of fibroid tissue on the wall of the uterus.

This condition is a cause of dysmenorrhea and infertility in women. The exact cause of this condition is poorly understood but evidence suggests that it is an inappropriate response of fibroid tissue to estrogen. Such a condition has been produced in rabbits by daily administrations of estrogen for 3 months. In guinea pigs, the condition has been produced by daily administration of estrogen for four months. Further, in rats, estrogen causes similar hypertrophy.

The most common treatment of uterine fibrosis involves surgical procedures both costly and sometimes a source of complications such as the formation of abdominal adhesions and infections. In some patients, initial surgery is only a temporary treatment and the fibroids regrow. In those cases a hysterectomy is performed which effectively ends the fibroids but also the reproductive life of the patient. Also, gonadotropin releasing hormone antagonists may be administered, yet their use is tempered by the fact they can lead to osteoporosis.

Endometriosis is a condition of severe dysmenorrhea, which is accompanied by severe pain, bleeding into the endometrial masses or peritoneal cavity and often leads to infertility. The cause of the symptoms of this condition appear to be ectopic endometrial growths which respond inappropriately to normal hormonal control and are located in inappropriate tissues. Because of the inappropriate locations for endometrial growth, the tissue seems to initiate local inflammatory-like responses causing macrophage infiltration and a cascade of events leading to initiation of the painful response. The exact etiology of this disease is not well understood and its treatment by hormonal therapy is diverse, poorly defined, and marked by numerous unwanted and perhaps dangerous side effects.

One of the treatments for this disease is the use of low dose estrogen to suppress endometrial growth through a negative feedback effect on central gonadotropin release and subsequent ovarian production of estrogen; however, it is sometimes necessary to use continuous estrogen to control the symptoms. This use of estrogen can often lead to undersirable side effects and even the risk of endometrial cancer.

Another treatment consists of continuous administration of progestins which induces amenorrhea and by suppressing ovarian estrogen production can cause regressions of the endometrial growths. The use of chronic progestin therapy is often accompanied by the unpleasant CNS side effects of progestins and often leads to infertility due to suppression of ovarian function.

A third treatment consists of the administration of weak androgens, which are effective in controlling the endometriosis; however, they induce severe masculinizing effects. Several of these treatments for endometriosis have also been implicated in causing a mild degree of bone loss with continued therapy. Therefore, new methods of treating endometriosis are desirable.

Aortal smooth muscle cell proliferation plays an important role in diseases such as atherosclerosis and restenosis. Vascular restenosis after PTCA has been shown to be a tissue response characterized by an early and late phase. The early phase occuring hours to days after PTCA is due to thrombosis with some vasospasms while the late phase appears to be dominated by excessive proliferation and migration of aortal smooth muscle cells. In this disease, the increased cell motility and colonization by such muscle cells and macrophages contribute significantly to the pathogenesis of the disease. The excessive proliferation and migration of vascular aortal smooth muscle cells may be the primary mechanism to the reocclusion of coronary arteries following PTCA, atherectomy, laser angioplasty and arterial bypass graft surgery. See "Intimal Proliferation of Smooth Muscle Cells as an Explanation for Recurrent Coronary Artery Stenosis after Percutaneous Transluminal Coronary Angioplasty," Austin et al., *Journal of the American College of Cardiology* 8: 369–375 (Aug. 1985).

Vascular restenosis remains a major long term complication following surgical intervention of blocked arteries by percutaneous transluminal coronary angioplasty (PTCA), atherectomy, laser angioplasty and arterial bypass graft surgery. In about 35% of the patients who undergo PTCA, reocclusion occurs within three to six months after the procedure. The current strategies for treating vascular restenosis include mechanical intervention by devices such as stents or pharmacologic therapies including heparin, low molecular weight heparin, coumarin, aspirin, fish oil, calcium antagonist, steroids, and prostacyclin. These strategies have failed to curb the reocclusion rate and have been ineffective for the treatment and prevention of vascular restenosis. See "Prevention of Restenosis after Percutaneous Transluminal Coronary Angioplasty: The Search for a 'Magic Bullet'", Hermans et al., *American Heart Journal* 122: 171–187 (July 1991).

In the pathogenesis of restenosis, excessive cell proliferation and migration occurs as a result of growth factors produced by cellular constituents in the blood and the damaged arterial vessel wall, which factors mediate the proliferation of smooth muscle cells in vascular restenosis.

Agents that inhibit the proliferation and/or migration of aortal smooth muscle cells are useful in the treatment and prevention of restenosis. The present invention provides for the use of compounds as aortal smooth muscle cell proliferation inhibitors and, thus, inhibitors of restenosis.

SUMMARY OF THE INVENTION

In its principal embodiment, the present invention provides a compound having the formula:

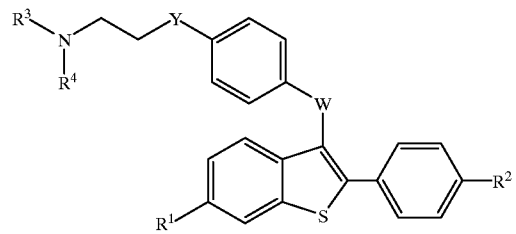

or a pharmaceutically acceptable salt thereof wherein $R^1$ and $R^2$ are independently selected from the group consisting of hydrogen, halo, hydroxy, —O(C–$C_6$ alkyl), —OC(O) ($C_1$–$C_6$ alkyl), —OC(O)O($C_1$–$C_6$ alkyl), —OC(O)Ar, —OC (O)OAr, and —OSO$_2$($C_4$–$C_6$ alkyl); where Ar is unsubstituted phenyl or is phenyl substituted with one or more substituents selected from the group consisting of alkyl of one to six carbon atoms, alkoxy of one to six carbon atoms, hydroxy, nitro, chloro, fluoro, trichloromethyl, and trifluoromethyl.

The linking group W is CHOH, C(O), or CH$_2$; and Y is —CH$_2$—, —NH—, —NMe—, —S—, or —SO$_2$—.

The substituents R$^3$ and R$^4$ are independently selected from the group consisting of H, alkyl of one to six carbon atoms, —C(O)(C$_1$–C$_6$ alkyl), —C(O)NH(C$_1$–C$_6$ alkyl), —C(O)Ar, where Ar is as defined above, or together with the nitrogen to which they are attached, R$^3$ and R$^4$ combine to form a 1-pyrrolidinyl, 1-piperidinyl, or a 5- or 6-membered imide or cyclic amide ring.

In a second embodiment, the present invention provides pharmaceutical compositions containing a therapeutically effective amount of a compound of formula I, optionally further comprising estrogen or progestin, in combination with a pharmaceutically acceptable carrier.

In yet another embodiment, the present invention comprises a method of treating osteoporosis, aortal smooth muscle cell proliferation, particularly restenosis, and estrogen-dependent cancer, particularly breast cancer.

DETAILED DESCRIPTION OF THE INVENTION

As used throughout this specification and the appended claims, the following terms have the indicated definitions.

The term "alkyl" refers to a monovalent radical derived by the removal of a single hydrogen atom from a straight or branched-chain saturated hydrocarbon. Alkyl groups include, for example, methyl, ethyl, propyl, isopropyl, butyl, n-butyl, pentyl, isopentyl, hexyl, isohexyl, and the like.

"Aryl," as used herein, means an unsubstituted phenyl group or a phenyl ring substituted with one or more substituents selected from alkyl of one to six carbon atoms, alkoxy of one to six carbon atoms, hydroxy, nitro, chloro, fluoro, trichloromethyl, and trifluoromethyl.

"Aryloxy" denotes an aryl grouop, as defined above, attached to the parent molecular moiety through an oxygen atom.

"Alkoxy" refers to an alkyl group as defined above, attached to the parent molecular moiety through an oxygen atom and is typified by groups such as methoxy, ethoxy, n-propoxy, isopropoxy, and the like.

"Alkoxycarbonyl" and "aryloxycarbonyl" denote, respectively, an alkoxy group or an aryloxy group, as defined above, attached to the parent molecular moiety through a carbonyl group.

"Alkoxycarbonyloxy" and "aryloxycarbonyloxy" mean, respectively, an alkoxycarbonyl group or an aryloxycarbonyl group, as defined above, attached to the parent molecular moiety through an oxygen atom.

The term "estrogen" includes steroidal compounds having estrogenic activity such as, for example, 17β-estradiol, estrone, conjugated estrogen (e.g., Premarin®), equine estrogen, 17α-ethynyl estradiol, and the like.

"Progestin" denotes compounds having progestational activity such as, for example, progesterone, norethynodrel, norgestrel, megestrol acetate, norethindrone, and the like.

Preferred compounds of this invention include compounds of formula I wherein W is —C(O)— and Y is —NH— or —S—.

Certain R$^3$ and R$^4$ groups also demonstrate preferable characteristics. For example, those compounds of formula I wherein R$^3$ and R$^4$ together with the nitrogen to which they are attached form 1-pyrrolidinyl or 1-piperidinyl are preferred. A further preferred subgroup of the preferred 1-pyrrolidinyl or 1-piperidinyl compounds include those compounds wherein R$^1$ and R$^2$ are —OH or —OCH$_3$.

Particularly preferred compounds of formula I include those having all of the aforementioned limitations, that is, compounds wherein W is C(O); Y is NH or S; R$^1$ and R$^2$ are —OH, —OC(O) (C$_1$–C$_6$ alkyl), —OC(O)O(C$_1$–C$_6$ alkyl), —OC(O)Ar, and —OC(O)OAr, especially —OH or —OCH$_3$, particularly wherein R$^1$ and R$^2$ are the same as one another; and R$^3$ and R$^4$, together with the nitrogen to which they are attached form 1-pyrrolidinyl or 1-piperidinyl.

Although the free-base or acid forms of formula I compounds can be used in the methods of the present invention, it is preferred to prepare and use a pharmaceutically acceptable salt form. Thus, the compounds used in the methods of this invention form pharmaceutically acceptable acid or base addition salts with a wide variety of organic and inorganic acids and bases, and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric, and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, b-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, terephthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. Preferred salts are the hydrochloride and oxalate salts.

Typical bases used to form pharmaceutically acceptable addition salts would be inorganic bases, such as, sodium hydroxide, potassium hydroxide, alkali carbonates or bicarbonates, calcium carbonate, magnesium carbonate, and the like. Additionally, organic bases may be utilized to form addition salts, e.g., alkyl amines, such as, triethylamine, dimethylamine, i-propylamine, and the like The pharmaceutically acceptable acid or base addition salts are typically formed by reacting a compound of formula I with an equimolar or excess amount of acid or base. The reactants are generally combined in a mutual solvent such as diethyl ether or ethyl acetate. The salt normally precipitates out of solution within about one hour to 10 days and can be isolated by filtration or the solvent can be stripped off by conventional means.

The pharmaceutically acceptable salts generally have enhanced solubility characteristics compared to the compound from which they are derived, and thus are often more amenable to formulation as liquids or emulsions.

Specific examples of compounds contemplated as falling within the scope of the present invention include, but are not limited to the following compounds and their pharmaceutically acceptable salts:

6-hydroxy-2-(4-hydroxyphenyl)-3-[(4-(2-(piperidin-1-yl) ethyl)thio)benzoyl]benzo[b]thiophene;

6-hydroxy-2-(4-hydroxyphenyl)-3-[(2-(4-piperidin-1-yl) ethyl)sulfonyl)benzoyl]benzo [b]thiophene;

6-methoxy-2-(4-methoxyphenyl)-3-[(4-(2-(piperidin-1-yl) ethyl)amino)benzoyl]benzo[b]thiophene;

6-methoxy-2-(4-methoxyphenyl)-3-[(4-(N-methyl-N-2-(piperidin-1-yl)ethyl)amino)benzoyl]benzo[b]thiophene;

6-methoxy-2-(4-methoxyphenyl)-3-[(4-(2-(piperidin-1-yl)ethyl)thio)benzoyl]benzo[b]thiophene; and 6-methoxy-2-(4-methoxyphenyl)-3-[(2-(4-piperidin-1-yl)ethyl)sulfonyl)benzoyl]benzo[b]thiophene.

The compounds of the present invention are derivatives of benzo[b]thiophene which is named and numbered according to the Ring Index, The American Chemical Society, as follows:

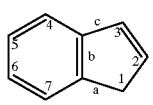

and are synthesized by methods detailed in Reaction Schemes 1 and 2 below.

In the synthetic sequence for preparing compounds of the present invention depicted in Reaction Scheme 1, compounds of the present invention are synthesized by first reacting a protected 6-hydroxy-2-(4-hydroxyphenyl)benzo[b]thiophene, 1, under Friedel-Crafts acylation conditions with an activated benzoyl derivative, 2, which is substituted in the 4-position with a suitable leaving group, L.

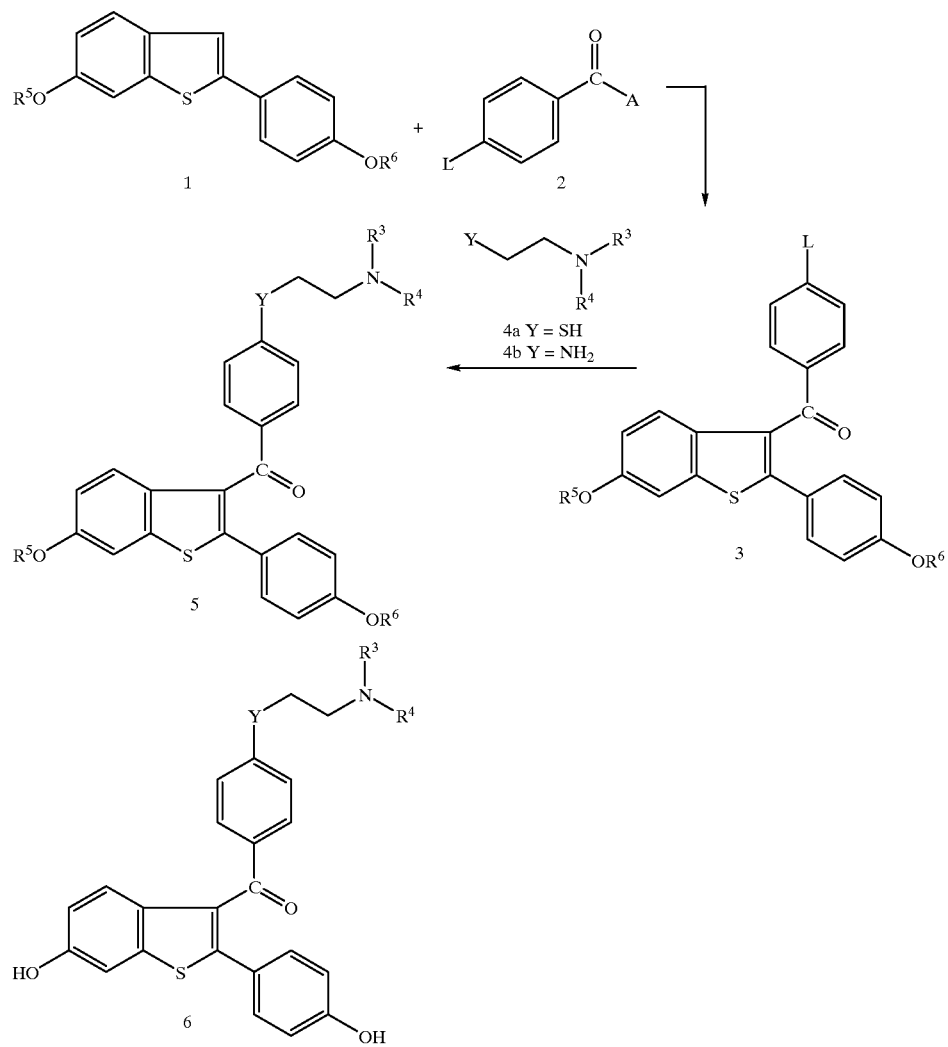

In compounds of formula 1, the protecting groups $R^5$ and $R^6$ are phenolic protecting groups capable of withstanding the conditions of the Friedel-Crafts acylation reaction and are of the type taught by T. Greene, et al. in Chapter 3 of "Protective Groups in Organic Synthesis," Second Edition, John Wiley & Sons, Inc., New York, 1991, pp.143–170. The preferred protecting groups are alkyl ether groups, with methyl being particularly preferred.

The leaving group, L, in compounds of formula 2 is selected from those groups known in the art to participate in nucleophilic aromatic substitution reactions (see J. March, "Advanced Organic Chemistry," 3rd Edition, John Wiley & Sons, New York, 1985, p. 587. Suitable leaving groups include fluoro, chloro, bromo, nitro, (lower alkyl)phenylsulfonyl, (lower alkyl)sulfonyl, phenylsulfonyl, azido, trialkylammonium, phenoxy, alkoxy, thioalkoxy, and amino.

For purposes of the present invention, the preferred leaving groups include fluoro, chloro, bromo, nitro, (lower alkyl)phenylsulfonyl, and lower alkylsulfonyl, with fluoro, bromo, and nitro being most preferred.

In compounds of formula 2, the activating group, A, is selected from groups well known in the art to activate acids for the purposes of carrying out Friedel-Crafts acylation reactions and include acid halides such as the fluoride, chloride and bromide; mixed acid anhydrides with $C_1$–$C_6$ alkanoic acids, $C_1$–$C_6$ alkylsulfonic acids, arylsulfonic acids, $C_1$–$C_6$ alkylsulfonic acids, perfluorinated $C_1$–$C_6$ alkanoic acids, $C_1$–$C_6$ alkylcarbonates, arylcarbonates, and the like. The preferred compounds of formula 2 are those in which A is halogen, most preferably chlorine.

Typically, the acylation reaction betrween 1 and 2 is carried out in an inert organic solvent in the presence of a Lewis acid catalyst. Suitable solvents include halogenated hydrocarbons such as dichloromethane, chloroform, 1,2-dichloroethane, carbon tetrachloride, chlorobenzene, dichlorobenzene and the like. The amount of solvent is not critical, but is generally sufficient to enable efficient mixing of the reaction components.

Suitable Lewis acid catalysts for the Friedel-Crafts acylation reaction between 1 and 2 include anhydrous aluminum, boron, or zinc halides with aluminum chloride being preferred.

Temperature and time of reaction will vary, depending upon the choice of reaction solvent, Lewis acid catalyst, and activating group, A. Generally, reactions are carried out at temperatures below or at ambient to below or at the reflux temperature of the solvent. Reaction times vary from several minutes to about forty-eight hours. The progress of the reaction toward completion can be followed by well-known techniques such as thin-layer chromatographic analysis of aliquots of the reaction mixture during the course of the reaction.

Typically, the reaction is conducted using 1.0 to 1.5 equivalents of compound 2 for each equivalent of protected benzo[b]thiophene, 1, with more of the activated benzoyl compound added during the course of the reaction as needed to drive the reaction to completion. The amount of Lewis acid catalyst employed ranges from between about 0.1 to 5 equivalents.

The product resulting from the acylation reaction, 3, is reacted next with a compound of formula 4 in which $R^3$ and $R^4$ have the meanings ascribed to them above. In the case where Y is —SH in compounds of formula 4a, the reaction between 3 and 4a is carried out by mixing the two reagents in the presence of a strong base in a polar aprotic solvent. Suitable strong bases include alkyllithiums, alkali metal amides, or metal hydrodies such as lithium, potassium or sodium hydride, or lithium aluminum hydride or sodium aluminum hydride.

Suitable polar aprotic solvents include N,N-dimethylformamide, N-methyl pyrrolidinone, N,N'-dimethylpropylurea, dimethylsulfoxide, tetrahydrofuran, and the like.

Alternatively, the sulfhydryl compound, 4a, can be separately converted to the corresponding anion by reaction with a strong base in a polar aprotic solvent, and the resulting anion subsequently reacted with compound 3.

In the case where Y is —$NH_2$, as in compound 4b, the preferred reaction conditions involve reaction of 3 with 4b in dimethylsulfoxide in the presence of the phase transfer reagent 18-crown-6 and 37% potassium fluoride adsorbed on alumina at a temperature of about 120_C.

Following the acylation reaction between compounds 3 and 4, the protecing groups of the resulting product, 5, are removed by methods taught in the art to produce the dihydroxy compounds 6 (for deprotection reagents and reaction conditions,see T. Greene, et al. cited above and the references cited therein). In the case where $R^5$ and $R^6$ are the preferred protecting group, methyl, the deprotective removal of the methyl groups can be carried out either by the use of an alkali metal ethanethionate (see G. I. Fetruell, et al., *Tetrahedron Letters,* 1327 (1970); idem. *Aust. J. Chem.,* 25: 1719 (1972) and A. S. Kende, et al., *Tetrahedron Letters,* 22: 1779 (1981) or by the use of either boron tribromide in methylene chloride at a temperature of between about −80_ C. to 20_C. for a period of 6–12 hours (J. F. W. McOmie, et al., *Org. Syn., Coll. Volume V,* 412 (1973)) or $BBr_3\cdot S$ $(CH_3)_2$ in ethylene chloride at a temperature of about 80_C. to 85_C (P. G. Williard, et al., *Tetrahedron Letters,* 21: 3731 (1981)).

Compounds of the present invention in which W is CHOH are prepared following deprotection step by dissolution in an appropriate solvent and reaction with reducing agent, such as, for example, lithium aluminum hydride, under an inert gas such as nitrogen.

A compound of the present invention wherein W is CHOH are further reduced to provide compounds in which W is methylene via standard procedures. This is accomplished by suspending the compound in an appropriate solvent and cooling under an inert gas such as nitrogen. To this suspension is added a suitable trialkyl silane reducing agent, preferably triethyl silyl, and a reasonably strong protic acid such as hydrochloric acid, trifluoroacetic acid, and the like.

When a —OC(O) ($C_1$–$C_6$ alkyl) or —OC(O)Ar group is desired at $R^1$ and $R^2$, a dihydroxy compound of formula I, is reacted with an agent such as acyl chloride, bromide, cyanide, or azide, or with an appropriate anhydride or mixed anhydride. The reactions are conveniently carried out in a basic solvent such as pyridine, lutidine, quinoline or isoquinoline, or in a tertiary amine solvent such as triethylamine, tributylamine, methylpiperidine, and the like. The reaction also may be carried out in an inert solvent such as ethyl acetate, dimethylformamide, dimethylsulfoxide, dioxane, dimethoxyethane, acetonitrile, acetone, methyl ethyl ketone, and the like, to which at least one equivalent of an acid scavenger, such as a tertiary amine, has been added. If desired, acylation catalysts such as 4-dimethylaminopyridine or 4-pyrollidinopyridine may be used. See, e.g., Haslam, et al., *Tetrahedron,* 36:2409–2433 (1980).

The acylation reactions which provide the aforementioned $R^1$ and $R^2$ groups are carried out at moderate temperatures in the range from about −25° C. to about 100° C., frequently under an inert atmosphere such as nitrogen gas. However, ambient temperature is usually adequate for the reaction.

Such acylations of the hydroxy group also may be performed by acid-catalyzed reactions of the appropriate carboxylic acids in inert organic solvents or neat. Acid catalysts such as sulfuric acid, polyphosphoric acid, methanesulfonic acid, and the like are used.

The aforementioned $R^1$ and $R^2$ groups also may be provided by forming an active ester of the appropriate acid, such as the esters formed by such known reagents as dicyclohexylcarbodiimide, acylimidazoles, nitrophenols, pentachlorophenol, N-hydroxysuccinimide, and 1-hydroxybenzotriazole. See, e.g., *Bull. Chem. Soc. Japan,* 38:1979 (1965), and *Chem. Ber.,* 788 and 2024 (1970).

When a compound is desired in which $R^1$ and $R^2$ is —$OSO_2$($C_4$–$C_6$ alkyl), the suitable starting dihydroxy compound is reacted with, for example, a derivative of the appropriate sulfonic acid such as a sulfonyl chloride, bromide, or sulfonyl ammonium salt, as taught by King and Monoir, *J. Am. Chem. Soc.,* 97:2566–2567 (1975). The dihydroxy compound also can be reacted with the appropriate sulfonic anhydride. Such reactions are carried out under conditions such as were explained above in the discussion of reaction with acid halides and the like.

Compounds of formula I can be prepared so that $R^1$ and $R^2$ are different biological protecting groups or, preferably, the same biological protecting group. Preferred protecting groups include —$CH_3$, —$C(O)C(CH_3)_3$, —$C(O)C_6H_5$, and —$SO_2(CH_2)_3CH_3$.

In an alternative synthetic sequence illustrated in Reaction Scheme 2 below, compounds of the present invention where Y is —S— or —$SO_2$— are prepared by first synthesizing the desired activated (4-substituted)benzoyl compound, 9, (the acid chloride being illustrated). The intermediate is prepared by converting the 4-substituted benzoic acid compounds, 7 to their corresponding amine substituted derivatives, 8. The substituted benzoic acids, 8 are converted to their corresponding acid chlorides, 9, by conventional methods known in the art.

The acid chlorides, 9, are reacted with a hydroxy-protected compound of formula 1 in a conventional Friedel-Crafts acylation reaction to produce the penultimate intermediates, 10. Deprotection (removal of groups $R^5$ and $R^6$ produces the desired compounds of the present invention in which Y is either —S— or —$SO_2$—.

Conversion of the aromatic hydroxy groups of compounds 11 to —OC(O) ($C_1$-$C_6$ alkyl), —OC(O)O($C_1$-$C_6$ alkyl), —O—C(O)Ar, —OC(O)OAr, and —$OSO_2$($C_4$-$C_6$ alkyl) is carried out in the manner described above.

Compounds of formula I can be prepared so that $R^1$ and $R^2$ are different biological protecting groups or, preferably, the same biological protecting group. Preferred protecting groups include $OCH_3$, O—C(O)—C($CH_3$)$_3$, O—C(O)—$C_6H_5$, and O—$SO_2$—($CH_2$)$_3$–$CH_3$.

The term "biological protecting groups" refers to those $R^1$ and $R^2$ substituents which delay, resist, or prohibit removal of such groups in a biological system such as, for example, following administration of a compound of the present invention containing the above-described $R^1$ and $R^2$ groups to a human. Such compounds also are useful for the methods herein described, especially when W is $CH_2$.

Reaction Scheme 2

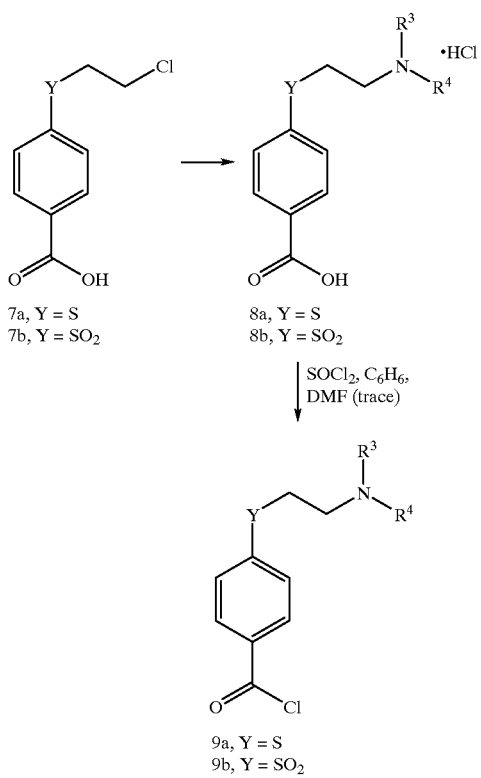

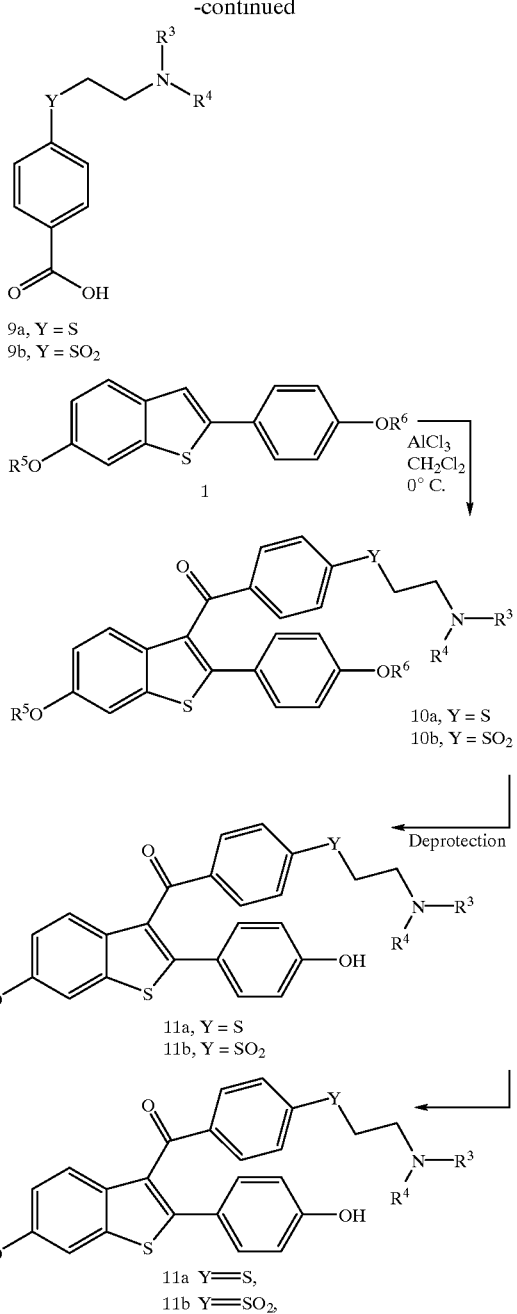

All reagents obtained from commercial sources were used without further purification unless otherwise indicated. $^1$H and $^{13}$C nuclear magnetic resonance spectra were measured as indicated at 300 and 75 MHz respectively. $^1$H-NMR chemical shifts are reported as δ values in ppm relative to the NMR solvent employed. $^1$H-NMR coupling constants are reported in Hertz (Hz) and refer to apparent multiplicities, indicated as follows: s (singlet), d (doublet), t (triplet), q (quartet), m (multiplet) and b (broad), in conjuction with "s", "d", "t" etc. Column chromatography was performed according to the method of Still et. al. (Still, W. C.; Kahn, M.; Mitra, A. *J. Org. Chem.* 1978, 43:2923) unless otherwise indicated with EM Science silica gel (230–400 mesh ASTM). In all cases, concentrations were performed under reduced pressure with a rotary evaporator.

The following preparations and examples are presented as representative embodiments of the present invention and are

PREPARATION OF INTERMEDIATES

Preparation 1

Preparation of 6-methoxy-2-(4-methoxyphenyl)-3-(4-nitrobenzoyl)benzo[b]thiophene To a slurry of 4-methoxy-2-(4-methoxyphenyl)benzo-[b]thiophene (1.00 g, 3.70 mmol) in 25 mL of dichloroethane at 5_C. was added 0.604 (4.52 mmol) of aluminum chloride. The slurry was observed to turn deep red. To this mixture was added 0.838 g (4.52 mmol) of 4-nitrobenzoyl chloride and the resulting mixture was stirred for one hour at 5_C. and then for three hours at room temperature. Additional aluminum chloride (0.2932 g, 2.215 mmol) and 4-nitrobenzoyl chloride (0.4065 g, 2.19 mmol) were added, and the resulting mixture stirred for three hours.

A final charge of aluminum chloride (0.272 g, 2.06 mmol) was added, and the resuting mixture stirred at room temperature for sixteen hours. At the end of this time, the reaction was quenched by addition of cold 1N hydrochloric acid and the reaction mixture was partitioned between ethyl acetate and 1N hydrochloric acid. The organic layer was separated, washed sequentially with water, saturated aqueous sodium bicarbonate, and saturated aqueous sodium chloride. The organic layer was collected, dried over anhydrous magnesium sulfate, filtered and concentrated to an oil which was then adsorbed on silica gel. Chromatography (2:1 hexanes:ethyl acetate) yielded 0.2744 g (18%) of the title compound as a solid, mp 168.9–170_C.

IR (KBr): 3140, 2820, 1659, 1603, 1528, 1347, 1251, 1045, 829 cm$^{-1}$.

$^1$H NMR (CDCl$_3$): δ 8.04 (d, 2H, J=8.9 Hz), 7.81 (m, 3H), 7.34 (d, 1H, J=2.3 Hz), 7.21 (d, 1H, J=8.7 Hz), 7.05 (dd, 1H, J=8.7), 6.69 (d, 2H, J=8.9 Hz), 3.91 (s, 3H), 3.71 (3H); $^{13}$C NMR (CDCl$_3$): 6192.0, 160.3, 158.0, 149.7, 147.2, 142.7, 140.2, 133.3, 130.8, 130.6, 129.1, 125.4, 124.3, 123.3, 115.3, 114.1, 104.5, 55.7, 55.3; Elemental Analysis: Calc'd. for C$_{23}$H$_{17}$NO$_5$S: C, 65.86; H 4.08: N, 3.34; S, 7.64; Found: C, 65.85; H, 4.11; N, 3.29; S, 7.51.

Preparation 2

Preparation of 6-methoxy-2-(4-methoxyphenyl)-3-(4-fluorobenzoyl)benzo[b]thiophene To a slurry of 4-methoxy-2-(4-methoxyphenyl)benzo-[b] thiophene (1.02 g, 3.77 mmol) in 25 mL of dichloroethane at 5_C. was added 0.600 (4.5 mmol) of aluminum chloride. The slurry was observed to turn deep red. To this mixture was added 0.535 mL (0.718 g, 4.52 mmol) of 4-fluorobenzoyl chloride and the resulting mixture was stirred for twenty-four hours at 5_C. and then quenched by addition of cold 20 mL of cold 1N hydrochloric acid. The reaction mixture was partitioned between dichloromethane and 1N hydrochloric acid. The organic layer was separated, and the aqueous layer was back extracted twice with dichloromethane. The organic layers were collected and washed saturated aqueous sodium chloride. The organic layer was collected, dried over anhydrous magnesium sulfate, filtered, concentrated and chromatographed on silica gel (8:1 hexanes:ethyl acetate) to yield 1.0879 g (74%) of the title compound as a solid, mp 108.1–109_C.

IR (KBr): 2980, 2940, 2810, 1640, 1598, 1473, 1251, 1152, 831 cm$^{-1}$. $^1$H NMR (CDCl$_3$): δ 7.78 (dd, 2H, J=5.6, 8.7 Hz), 7.61 (d, 1H, J=8.9 Hz),7.28 (m, 3H), 6.98 (dd, 1H, J=2.5, 8.9 Hz), 6.94 (m, 3H), 6.72 (d, 2H, J=8.7 Hz), 3.88 (s, 3H), 3.73 (3H); $^{13}$C NMR (CDCl$_3$): 6192.8, 167.4, 164.0, 160.0, 157.9, 144.3, 140.2, 134.0, 133.9, 133.8, 132.7, 132.5, 130.6, 130.0, 125.8, 124.2, 115.7, 115.5, 115.1, 114.1, 104.6, 55.7, 55.3; $^{19}$F NMR (CDCl$_3$): δ 48.31 (t, J=6 Hz); Elemental Analysis: Calc'd. for C$_{23}$H$_{17}$FO$_3$S: C, 70.39; H, 4.37; S, 8.17; F, 4.84; Found: C, 70.21; H, 4.38;, S, 8.27; F, 5.14.

Preparation 3

Preparation of 6-methoxy-2-(4-methoxyphenyl)-3-(4-bromobenzoyl)benzo [b]thiophene To a slurry of 4-methoxy-2-(4-methoxyphenyl)benzo-[b] thiophene (0.99 g, 3.66 mmol) in 25 mL of dichloroethane at 5_C. was added 0.622 g (4.66 mmol) of aluminum chloride. The slurry was observed to turn deep red. To this mixture was added (0.997 g, 4.54 mmol) of 4-bromobenzoyl chloride and the resulting mixture was stirred for three hours at 5_C. and then quenched by addition of cold 10 mL of cold 1N hydrochloric acid. The reaction mixture was partitioned between ethyl acetate and 1N hydrochloric acid. The organic layer was separated, and washed sequentially with saturated aqueous sodium bicarbonate and saturated aqueous sodium chloride. The organic layer was collected, dried over anhydrous magnesium sulfate, filtered, concentrated to an oil and chromatographed on silica gel (9:1 hexanes:ethyl acetate) to yield several fractions containing product. These fractions were combined, concentrated, and dried in vacuo at 100_C. overnight to yield 1.0715 g (65%) of the title compound as a viscous oil.

IR (CHCl$_3$): 3030,1647, 1608, 1586, 1477, 1253, 831 cm$^{-1}$. $^1$H NMR (CDCl$_3$): δ 7.61 (m, 3H), 7.33 (m, 5H),6.98 (dd, 1H, J=8.7, 2.1 Hz), 6.71 (d, 2H, J=8.7 Hz), 3.83 (s, 3H), 3.69 (s, 3H), 3.69 (s, 3H); $^{13}$C NMR (CDCl$_3$): δ 193.2, 160.1, 157.9, 144.7, 140.2, 136.4, 133.7, 131.7, 131.4, 130.6, 129.7, 128.3, 125.8, 124.2, 115.1, 114.2, 104.6, 55.7, 55.4;

A portion of the product material was recrystallized from ethyl acetate to obtain a sample for elemental analysis.

Elemental Analysis: Calc'd. for C$_{23}$H$_{17}$BrO$_3$S: C, 60.94; H, 3.78; S, 7.07; Br, 17.62; Found: C, 61.14; H, 3.93;, S, 6.94; Br, 17.79.

PREPARATION OF COMPOUNDS OF THE INVENTION

EXAMPLE 1

Preparation of 6-methoxy-2-(4-methoxyphenyl)-3-[(4-(2-(piperidin-1-yl)ethyl)amino)benzoyl]benzo[b]thiophene

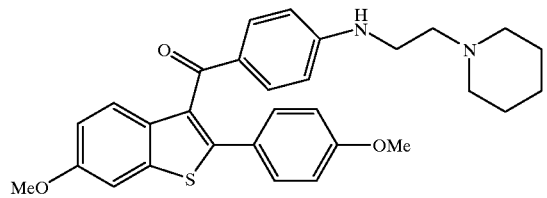

Step a) Preparation of 6-methoxy-2-(4-methoxyphenyl)-3-(4-fluorobenzoyl)benzo [b]thiophene To a slurry of 6-methoxy-2-(4-methoxyphenyl)-benzo[b] thiophene (1.02 g, 3.77 mmol) in dichloromethane (25 mL) at 5_C. was added aluminum trichloride (0.600 g, 4.5 mmol). The slurry was observed to turn deep red. To this mixture was added p-fluorobenzoyl chloride (0.535 mL, 0.718 g, 4.52 mmol). The resulting mixture was stirred for 24 h at 5C, then quenched by addition of cold 1N HCl (20 mL) and partitioned between dichloromethane and 1N HCl. The aqueous layer was back extracted twice with dichloromethane, and the organics were washed with saturated aqueous NaCl and dried (MgSO$_4$). Following filtration and concentration, the residue was chromatographed on silica gel (8:1 hexanes:ethyl acetate) to afford 1.09 g (74%) of the title compound as a solid, mp=108.1–109.0_C.

Infrared: (KBr) 2980, 2940, 2810, 1640, 1598, 1473, 1251, 1152, 831 cm$^{-1}$; $^1$H NMR (CDCl$_3$) δ 7.78 (dd, 2 H, J=5.6, 8.7 Hz), 7.61 (d, 1 H, J=8.9 Hz), 7.28 (m, 3 H), 6.98 (dd, 1 H, J=2.5, 8.9 Hz), 6.94 (m, 3 H), 6.72 (d, 2 H, J=8.7 Hz), 3.88 (s, 3 H), 3.73 (s, 3 H); $^{13}$C NMR (CDCl$_3$) δ 192.8, 167.4, 164.0, 160.0, 157.9, 144.3, 140.2, 134.0, 133.9, 133.8, 132.7, 132.5, 130.6, 130.0, 125.8, 124.2, 115.7, 115.5, 115.1, 114.1, 104.6, 55.7, 55.3; $^{19}$F NMR (CDCl$_3$) 6 48.31 (t, J=6 Hz) Elemental Analysis: Calcd. for C$_{23}$H$_{17}$FO$_3$S: C, 70.39; H, 4.37; S, 8.17; F, 4.84. Found: C, 70.21; H, 4.38; S, 8.27; F, 5.14.

Step b) Preparation of 6-methoxy-2-(4-methoxyphenyl)-3-[4-(2-(piperidin-1-yl)ethylamino)benzoyl]-benzo[b]thiophene

[6-Methoxy-2-(4-methoxyphenyl)-3-(4-fluorobenzoyl)] benzothiophene (0.2 g, 0.51 mmol, prepared as described in Step a) above) was stirred in DMSO (0.33 g, 4.08 mmol) and 1-(2-aminoethyl)piperidine (0.065 g, 0.51 mmol), 18-crown-6 (0.014 g, 0.051 mmol) and 37% KF/Alumina (0.11 g, 0.68 mmol) was added. The reaction was heated to 125° C. and allowed to stir overnight. The reaction was then cooled to room temperature and quenched with H$_2$O. It was extracted with EtOAc and washed with H$_2$O (3×) followed by brine (1×). The organic layer was dried with MgSO$_4$, filtered and concentrated under reduced pressure. The crude product was purified by column chromatography (5% MeOH/MeCl$_2$) to afford 0.18 g (72%) the title compound.

$^1$H NMR (300 MHz, MeOD d$_4$) : δ 7.68 (d, 2H, J=8.8 Hz), 7.43 (m, 3H), 7.29 (d, 1H, J=2.2 Hz), 6.91 (dd, 1H, J=8.8,2.2 Hz), 6.77 (d, 2H, J=8.8 Hz), 6.41 (d, 2H, J=8.8 Hz), 5.10(t, 1H, J=4 Hz), 3.87 (s, 3H), 3.74 (s, 3H), 3.13 (m, 2H), 2.51 (m, 2H), 2.36 (br, 4H), 1.55(br, 4H), 1.43 (br, 2H); FD+ MS for C$_{30}$H$_{32}$N$_2$O$_3$S=500; Elemental Analysis: Calcd. for C$_{30}$H$_{32}$N$_2$O$_3$S: C, 71.97; H, 6.44; N, 5.50; Found: C, 72.17; H, 6.28; N, 5.39.

EXAMPLE 2

Preparation of 6-hydroxy-2-(4-hydroxyphenyl)-3-[(4-(2-(piperidin-1-yl)ethylamino)benzoyl]benzo[b]thiophene;

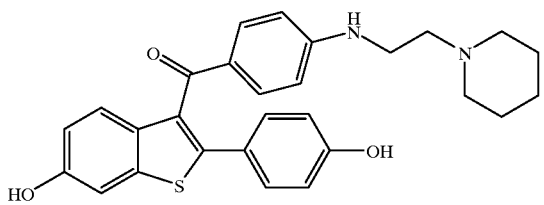

6-Methoxy-2-(4-methoxyphenyl)-3-[4-(2-(piperidin-1-yl)ethyl)amino)benzoyl]benzo [b]thiophene (prepared as described in Step b) above was converted to the hydrochloride salt and the resulting product stirred in EtCl$_2$ at 5° C. BBr$_3$ was added and the reaction mixture was stirred for 5 hours at 5° C. It was then poured into cold H$_2$O and extracted with EtCl$_2$ followed by extraction with EtOAc. The organic layers were combined and concentrated under reduced pressure. The crude product was purified by column chromatography (15% MeOH/MeCl$_2$) to afford 0.08 g (74%) of the title compound, isolated as the hydrochloride salt.

$^1$H NMR (300 MHz, MeOD d4) d 7.59 (d, 2H, J=8.8 Hz), 7.34 (d, 1H, J=8.8 Hz), 7.24 (m, 3H), 6.84 (dd, 1H, J=8.8, 2.6 Hz), 6.66 (d, 2H, J=8.8 Hz), 6.49 (d, 2H,J=8.8 Hz), 3.32 (m, 2H), 2.65 (m, 6H), 1.66 (m, 4H), 1.52 (m, 2H); FD+ MS for C$_{28}$H$_{28}$N$_2$O$_3$S=472; Elemental Analysis: Calcd. for C$_{28}$H$_{28}$N$_2$O$_3$SΩ0.5 HCl: C, 68.52; H, 5.85; N, 5.71; Found: C, 68.45; H, 5.96; N, 5.53.

EXAMPLE 3

Preparation of 6-methoxy-2-(4-methoxyphenyl)-3-[4-(2-(piperidin-1-yl)ethylthio)benzoyl]benzo[b]thiophene

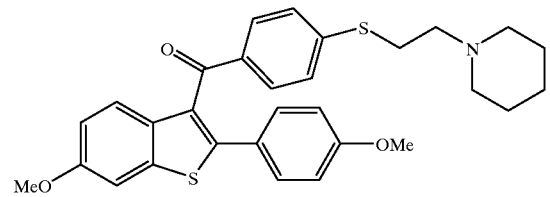

Step a) Preparation of 2-(piperidin-1-yl)ethanethiol

Thiourea (6.0 g, 78.8 mmol) was stirred in anhydrous EtOH (25 ml) and 1-(2-chloroethyl) piperidine hydrochloride (14.2 g, 77.3 mmol) in anhydrous EtOH (50 ml) was added slowly over 20 min. via an addition funnel. The resulting solution was heated under reflux overnight. The ethanol was removed under reduced pressure. Ethanol (60 ml) was added followed by a solution of 77 mL of ethyl acetate and 20 mL of petroleum Ether. The product crystalized and was filtered. Some of this intermediate (4.36 g, 19.4 mmol) was dissolved in H$_2$O (10 ml) and NaOH(1.09g, 27.2 mmol) in H$_2$O (4.8 ml) was added. The mixture was heated with heat gun until a slight red oily layer could be detected. The organics were extracted with Et$_2$O, dried with MgSO$_4$, filtered. The ether layer contained the title product which was used without further purification.

Step b) Preparation of 6-methoxy-2-(4-methoxyphenyl)-3-[4-(2-(piperidin-1-yl)ethylthio)benzoyl]-benzo[b]thiophene 2-(Piperidin-1-yl)ethanethiol (2.8 g, 19.2 mmol, prepared as described in Step a) above) was stirred in 50 mL of diethyl ether under nitrogen at 0° C. and NaH (0.676g of 60% dispersion in mineral oil) was added. The resulting solution was allowed to stir for 20 minutes. 6-Methoxy-2-(4-methoxyphenyl)-3-(4-fluorobenzoyl)benzo [b]thiophene (0.94 g, 2.40 mmol, prepared as described in Example 1, Step a) above) in 100 mL of DMF was added. The reaction mixture was heated to reflux and stirred for 1 hour. The crude mixture was then poured into H$_2$O and extracted three times with EtOAc. The organic layer was washed with brine, dried with MgSO$_4$, filtered, and concentrated under reduced pressure. The crude product was purified by column chromatography (10% MeOH/MeCl$_2$) to afford 1.3 g (98%) of the title compound.

$^1$H NMR (300 MHz, CDCl$_3$) δ 7.72 (d, 2H, J=8.5 Hz), 7.60 (d, 1H, J=8.8 Hz), 7.34–7.24 (complex m, 5H), 6.69 (dd, 1H, J=8.8, 2.2 Hz), 6.76 (d, 2H, J=8.8 Hz), 3.90 (s, 3H), 3.76 (s, 3H), 3.56 (m, 4H), 3.01 (m, 2H), 2.58 (m, 2H), 2.29 (m, 2H), 1.88 (m, 3H), 1.43–1.34 (m, 1H). FD+ MS for C$_{30}$H$_{32}$NO$_3$S$_2$Cl=517. Elemental Analysis: Calcd. for C$_{30}$H$_{32}$NO$_3$S$_2$Cl: C, 65.02; H, 5.82; N, 2.S3; Found: C, 65.27; H, 6.01; N, 2.66.

EXAMPLE 4

Preparation of 6-hydroxy-2-(4-hydroxyphenyl)-3-[4-(2-(piperidin-1-yl)ethylthio)benzoyl]-benzo[b]thiophene

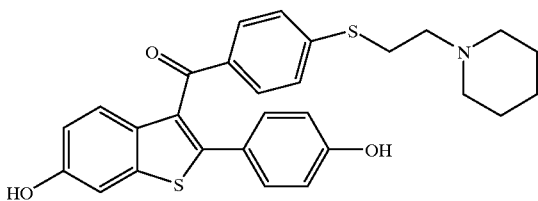

6-Methoxy-2-(4-methoxyphenyl)-3-[4-(2-(piperidin-1-yl)-ethylthio)benzoyl]benzo[b]thiophene (0.50 g, 0.90 mmol, prepared as described in Step b) above) was dissolved in 10 mL of dichloromethane at 0° C. and $BBr_3$ (3.6 ml of 1M, 3.6 mmol) was added. The resulting reaction mixture was stirred for 2 hours. The reaction mixture was then poured into $H_2O$ and sufficient $NaHCO_3$ was added to keep pH between 7–9. It was extracted with ethyl acetate, dried with $MgSO_4$, filtered, and concentrated under reduced pressure. The crude product was purified by column chromatography (10% $MeOH/MeCl_2$) to afford 0.13 g (29%) of the title compound. $^1$H NMR (300 MHz, $CDCl_3$): δ 7.69 (d, 1H, J=8.8 Hz), 7.59 (d, 2H, J=8.5 Hz), 7.29 (d, 1H, J=2.2), 7.16 (d, 2H, J=8.5 Hz), 7.11 (d, 2H, J=8.8 Hz), 6.95 (dd, 1H, J=8.8, 2.2 Hz), 6.58 (d, 2H, J=8.8 Hz), 2.96 (br, 2H), 2.58 (m, 6H), 1.62 (br, 4H), 1.47 (br, 2H); FD+ MS for $C_{28}H_{27}NO_3S_2$=489; Elemental Analysis: Calcd. for $C_{28}H_{27}NO_3S_2$: C, 68.68; H, 5.56; N, 2.86; Found: C, 68.86; H, 5.79; N, 2.88.

EXAMPLE 5

Preparation of 6-methoxy-2-(4-methoxyphenyl)-3-[4-(N-methyl-N-2-(piperidin-1-yl)ethylamino)benzoyl]-benzo[b]thiophene

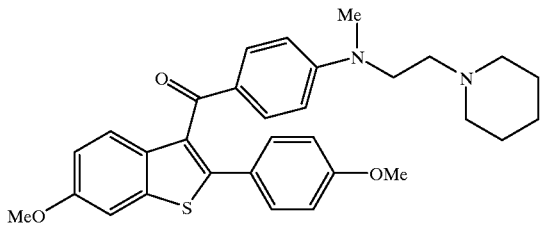

Step a) Preparation of 4-[(N-methyl-N-(2-piperidin-1-yl)-ethyl)amino]benzoic acid, methyl ester Methyl p-N-methylaminobenzoate (0.5 g, 3.31 mmol) was stirred in THF (5 ml) at 0° C. under nitrogen. NaH was added. This was stirred for 15 min. and the ice bath was removed. 1-(2-chloroethyl) piperidine (0.54 g, 3.64 mmol) was added in minimal THF. The reaction was stirred at reflux for 48 hours. It was cooled to room temperature, quenched with water and extracted with EtOAc. The organic layer was dried with $MgSO_4$, filtered and concentrated under reduced pressure. The crude product was purified by column chromatography (5% MeOH/MeCl2) to afford 0.42g (46%) of 7.

$^1$H NMR (300 MHz, $CDCl_3$): δ 7.94 (d, 2H, J=8.8 Hz), 6.91 (d, 2H, J=8.8 Hz), 4.12 (t, 2H, J=7.3 Hz), 3.84 (s, 3H), 3.53 (t, 2H, J=7.3 Hz), 3.02 (s, 3H), 2.80 (br, 4H), 1.75 (br, 4H), 1.60 (br, 2H); FD+ MS for $C_{16}H_{24}N_2O_2$=276.2.

Step b) Preparation of 4-[(N-methyl-N-(2-piperidin-1-yl)-ethyl)amino]benzoic acid 4-[(N-Methyl-N-(2-piperidin-1-yl)ethyl)amino]benzoic acid, methyl ester (0.40 g, 1.43 mmol, prepared as described in Step a) above) was heated under reflux for two hours in 20 mL of 5N NaOH. The condenser was removed to allow the methanol to escape and heating under reflux was continued overnight. The reaction was acidified with HCl, $H_2O$ was removed and the resulting 4-[(N-methyl-N-(2-piperidin-1-yl)ethyl)amino]benzoic acid was taken directly on to the next step without further purification.

Step c) Preparation of 6-methoxy-2-(4-methoxyphenyl)-3-[4-(N-methyl-N-2-(piperidin-1-yl)ethylamino)benzoyl]-benzo[b]thiophene 4-[(N-Methyl-N-(2-piperidin-1-yl)ethyl)amino]benzoic acid (0.43 g, 1.43 mmol, prepared as described in Step b) above) was stirred in 1:1 toluene (10 ml)/$MeCl_2$ (10 ml), thionyl chloride (0.84 g, 7.15 mmol), and cat. DMF (1 drop). The reaction was stirred and heated under reflux overnight. The solvents were removed under reduced pressure. The crude acid chloride was triturated with $Et_2O$. 6-Methoxy-2-(4-methoxyphenyl)-benzo[b]thiophene (0.35 g, 1.30 mmol) and the acid chloride (1.43 mmol) were suspended in dichloromethane and $AlCl_3$ (0.87 g, 6.50 mmol) was added. The reaction was stirred at room temperature for 3 hours. It was quenched with cold $H_2O$ (10 ml) and the solvents were removed under reduced pressure. The crude mixture was taken up in MeOH saturated with HCl and refluxed. The MeOH was then removed and the solid was triturated with $H_2O$. The crude product was purified by column chromatography (5% $MeOH/MeCl_2$) to afford 0.23g (35%) of the title compound. $^1$H NMR (300 MHz, $CDCl_3$) : δ 7.65 (d, 2H, J=8.8 Hz), 7.31 (d, 1H, J=8.8 Hz), 7.21 (m, 3H), 6.82 (d, 1H, J=8.8 Hz), 6.62 (d, 2H, J=8.6 Hz), 3.93 (s, 3H), 3.87 (t, 2H, J=7.3 Hz), 3.74 (s, 3H), 3.00 (s, 3H), 2.80 (br, 6H), 1.75 (br, 4H), 1.60 (br, 2H); FD+ MS for $C_{31}H_{34}N_2O_3S$=514; Elemental Analysis: Calcd. for $C_{31}H_{34}N_2O_3S$: C, 72.34; H, 6.66; N, 5.44; Found: C, 72.09; H, 6.63; N, 5.19.

EXAMPLE 6

Preparation of 6-hydroxy-2-(4-hydroxyphenyl)-3-[4-(N-methyl-N-2-(piperidin-1-yl)ethylamino)benzoyl]-benzo[b]thiophene

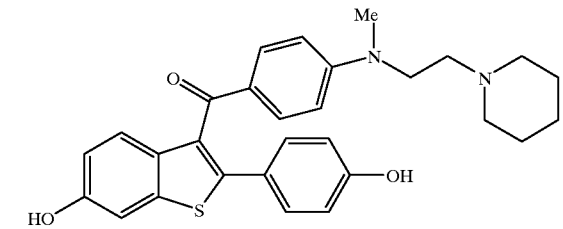

6-Methoxy-2-(4-methoxyphenyl)-3-[4-(N-methyl-N-2-(piperidin-1-yl)ethylamino)benzoyl]benzo[b]thiophene (0.191 g, 0.379 mmol, prepared as described in Example 3 above) was dissolved in 20 mL of dichloroethane and $BBr_3 \cdot SMe_2$ (0.71 g, 2.27 mmol) was added. The reaction was heated to 83° C. for 24 hours. The reaction was quenched with $H_2O$ (10 ml), the organic layer was removed and the aqueous layer extracted with ethyl acetate. The crude product was purified by column chromatography (15% $MeOH/MeCl_2$) to afford 0.118 g (66%) of the free base of the title compound. The hydrochloride salt was formed with methanolic hydrogen chloride, isolated by filtration and vacuum dried.

$^1$H NMR (300 MHz, $CDCl_3$) δ 7.65 (d, 2H, J=8.8 Hz), 7.31 (d, 1H, J=8.8 Hz), 7.20 (m, 3H), 6.82 (d, 1H, J=8.8 Hz), 6.63 (d, 2H, J=8.6 Hz), 3.87 (t, 2H, J=7.3 Hz), 3.02 (s, 3H), 2.80 (br, 6H), 1.75 (br, 4H), 1.60 (br, 2H); FD+ MS for $C_{29}H_{30}N_2O_3S$=486; Elemental Analysis: Calcd. for $C_{29}H_{30}N_2O_3S \cdot 0.8$ HCl: C, 63.17; H, 5.63; N, 5.08; Found: C, 62.95; H, 5.77; N, 4.91.

EXAMPLE 7

Preparation of 6-methoxy-2-(4-methoxyphenyl)-3-[4-(2-(piperidin-1-yl)ethylsulfonyl)benzoyl]benzo[b]thiophene

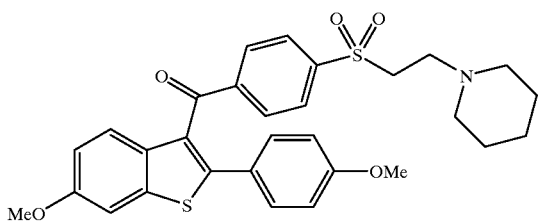

Step a) Preparation of 4-(2-(piperidin-1-yl)ethyl) sulfonylbenzoic acid

A solution of 5g (20 mmol) p-carboxyphenyl 2-chloroethyl sulfone (prepared by the method of Shiniriki and Nambara; Chem. Pharm. Bull. (Tokyo), 11, 178–183, 1963) in 30 ml piperidine plus 10 ml dimethylformamide was heated to 120_C. for one hour. The mixture was cooled to room temperature and triturated with 100 mL of ether and the solids were removed by filtration. The solids were dissolved in 200 mL 1N sodium hydroxide and washed with ether (2×200 mL). The aqueous layer was acidified with 60 ml 1N HCl and ether extracted (2×200 mL). The aqueous layer was stripped under reduced pressure and the resulting sticky white solid was recrystalized from water affording 3.9 g (58% yield) of the title compound as white plates.

$^1$H NMR (300 MHz, $D_6$-DMSO): δ 13.5 (bs, 1H), 11.4 (bs, 1H), 8.23 (d, 2H, J=8.5Hz), 8.08 (d, 2H, J=8.5 Hz), 4.12 (m, 2H), 3.40 (bs, 2H), 3.30 (m, 2H), 2.89 (bs, 2H), 1.76 (m, 5H), 1.36 (br, 1H); $^{13}$C-NMR (300 MHz, $D_6$-DMSO): δ 166.0, 141.6, 135.9, 130.4, 128.2, 52.0, 49.0, 48.6, 22.3, 21.2; FAB-MS for $C_{13}H_{20}NO_4S$ (M*+1)=298.1 (free base); Elemental Analysis: Calcd. for $C_{14}H_{20}NO_4SCl$: C, 50.37; H, 6.04; N, 4.20; O, 19.17; S, 9.60; Cl, 10.62; Found: C, 50.79; H, 6.16; N, 4.06; 0, 20.47; S, 8.81; Cl, 10.11.

Step b) Preparation of 6-methoxy-2-(4-methoxyphenyl)-3-[4-(2-(piperidin-1-yl)ethylsulfonyl)benzoyl]benzo[b]thiophene To a solution of 1.6 g (4.8mmol) of 4-(2-(piperidin-1-yl) ethyl)sulfonylbenzoic acid (prepared as described in Step a) above) in 150 mL $MeCl_2$ was added 1 drop of dimethylformamide and 2.1 ml thionyl chloride. The resulting solution was stirred overnight at room temperature under a dry atmosphere. An additional 1 drop of dimethylformamide and 1 ml thionyl chloride was added and the mixture was heated under reflux for six hours. After cooling, the solvents were removed under reduced pressure and the crude acid chloride was resuspended in 150 mL toluene and stripped again twice. The solid was triturated with ether (2×50 mL) and dried under vacuum. The resulting off-white solid was resuspended in 200 ml methylene chloride and 1.92 g (14.4 mmol, 3 eq.) aluminum chloride and 1.42 g (5.3 mmol, 1.1 eq.) 6-methoxy-2-(4-methoxyphenyl)benzo[b]thiophene was added and the solution was stirred overnight at room temperature under a dry nitrogen atmosphere. The reaction was quenched with 2 ml 5% sodium bicarbonate plus 200 ml water and the organic layer was separated. The aqueous layer was extracted with ethyl acetate (200 ml). The combined organic layers were dried ($MgSO_4$) and stripped. The crude product was chromatographed on silica gel using a zero to 6% methanol in $MeCl_2$ gradient over 60 minutes. The product was taken up in 120 ml of 1:1 ether/ethyl acetate and hydrogen chloride was bubbled through the solution. The resulting precipitate was isolate by filtration and vacuum dried. The hydrochloride salt was digested in 75 mL methanol plus 50ml ethyl acetate hot then cooled to 5_C. and isolated by filtration and vacuum drying affording 1.22 g (43%) the title compound as a bright yellow solid.

$^1$H NMR (300 MHz, $D_6$-DMSO/$CDCl_3$): δ 12.2 (bs, 1H), 7.88 (d, 2H, J=8.5 Hz), 7.82 (d, 2H, J=8.5 Hz), 7.74 (d, 1H, J =8.8 Hz), 7.36 (d, 1H, J=2.6 Hz), 7.22 (d, 2H, J=8.8 Hz), 7.04 (dd, 1H, J=2.6, 8.8 Hz), 6.73 (d, 2H, J =8.8 Hz), 3.95 (m, 2H), 3.91 (s, 3H), 3.75 (s, 3H), 3.49 (bd, 2H, J=11.4 Hz), 3.31 (m, 2H), 2.94 (bs, 1H), 2.81 (bq, 2H, J=11.8 Hz), 2.13 (bq, 2H, J=13.2 Hz), 1.85 (bd, 3H, J=11.8 Hz), 1.42 (bq, 1H, J=12.9 Hz); FAB-MS for $C_{30}H_{31}NO_5S_2$ (M*+1)=550.0 (free base); Elemental Analysis: Calcd. for $C_{30}H_{32}NO_5S_2Cl$: C, 61.47; H, 5.50; N, 2.39; Cl, 6.05; 0, 13.65; S, 10.94; Found: C, 61.64; H, 5.57; N, 2.60; Cl, 5.90; 0, 13.56; S, 10.82.

EXAMPLE 8

Preparation of 6-hydroxy-2-(4-hydroxyphenyl)-3-[4-(2-(piperidin-1-yl)ethylsulfonyl)benzoyl]benzo[b]thiophene

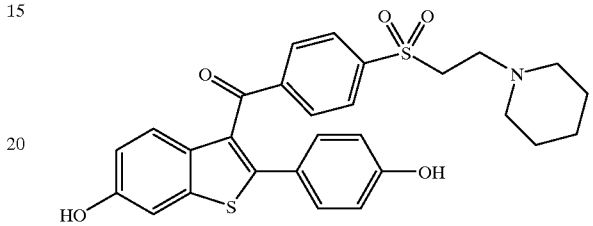

Aluminum chloride (1.45 g, 10.9 mmol, 8 eq.) was added to a solution of 0.81 mL (10.9 mmol, 8 eq.) of ethanethiol in 25 mL dry $EtCl_2$ under a dry atmosphere. After stirring for 10 minutes a solution of 800 mg (1.36 mmol, 1 eq.) 6-methoxy-2-(4-ethoxyphenyl)-3-[4-(2-(piperidin-1-yl) ethylsulfonyl)-benzoyl]benzo[b]thiophene in 25 mL $EtCl_2$ was added and the mixture was stirred for 3 hours at room temperature. The reaction was quenched with 10ml 5% sodium bicarbonate, 100 mL water and 200 mL ethyl acetate. The organic layer was removed and the aqueous layer was extracted with ethyl acetate (2×200ml). The combined organic layers were dried ($MgSO_4$) and the solvents were removed under reduced pressure. The crude product was purified by silica gel chromatography using a zero to 10% methanol in $MeCl_2$ gradient in 30 minutes affording 631mg (89%) of the title compound as a bright yellow solid.

$^1$H NMR (300 MHz, $D_6$-DMSO): δ 9.82 (bs, 2H), 7.84 (s, 4H), 7.46 (d, 1H, J 8.8 Hz), 7.38 (d, 1H, J=2.2 Hz), 7.13(d, 2H, J=8.5 Hz), 6.90 (dd, 1H, J=2.2, 8.8 Hz), 6.62 (d, 2H, J=8.5 Hz), 3.47 (t, 2H, J=6.7 Hz), 2.45 (t, 2H, J=6.7 Hz), 2.14 (bs, 4H), 1.21 (bs, 6H); FAB-MS for $C_{28}H_{27}NO_5S_2$ (M*+1)=522.1; Elemental Analysis: Calcd. for $C_{28}H_{27}NO_5S_2$: C, 64.47; H, 5.22; N, 2.69; O, 15.34; S, 12.29; Found: C, 64.75; H, 5.36; N, 2.47; O, 15.46; S, 12.04. UV/VIS (methanol) k (extinction) 204 (32,000), 236 (32, 000), 295 (17,000), 375 (2860).

The compounds of formula I of the present invention are useful for alleviating the symptoms of hyperlipidemia, estrogen-dependent cancer, particularly estrogen-dependent breast and uterine carcinoma, and the conditions of osteoporosis, and cardiovascular diseases, particularly when the latter two conditions are associated with post-menapousal syndrome.

The terms "alleviating" or "treating" are defined to include prophylactic treatment of a person at risk of incurring one or more symptoms or pathological conditions listed above, holding in check such symptoms or pathological conditions, and treating existing symptoms or pathological conditions, as appropriate.

Compounds of the present invention are also effective for inhibiting uterine fibroid disease and endometriosis in women, and smooth muscle cell proliferation in humans. The following non-limiting biological test examples illustrate the methods of the present invention.

BIOLOGICAL TEST PROCEDURES

I. General Preparation for Post-Menopausal Rat Model

In the examples illustrating the methods, a post-menopausal model was used in which effects of different treatments upon various biological parameters were determined, including serum cholesterol concentration, uterine weight, estrogen receptor binding, uterine eosinophil peroxidase activity, MCF-7 cell proliferation, and bone density.

Seventy-five day old female Sprague Dawley rats (weight range of 200 to 225 g) were obtained from Charles River Laboratories (Portage, Mich.). The animals were either bilaterally ovariectomized (OVX) or exposed to a sham surgical procedure (Intact) at Charles River Laboratories, and then shipped after one week. Upon arrival, they were housed in metal hanging cages in groups of 3 or 4 per cage and had ad libi tum access to food (calcium content approximately 0.5%) and water for one week. Room temperature was maintained at 22.20°±1.70° C. with a minimum relative humidity of 40%. The photoperiod in the room was 12 hours light and 12 hours dark.

II. Four Day Dosing Regimen

After a one week acclimation period (therefore, two weeks post-OVX), daily dosing with test compound was initiated. 17a-Ethynyl estradiol ($EE_2$) (Sigma Chemical Co., St. Louis, Mo.), an orally available form of estrogen, or the test compound were given orally, unless otherwise stated, as a suspension in 1% carboxymethyl cellulose or dissolved in 20% β-cyclodextrin. Animals were dosed daily for 4 days. Following the dosing regimen, animals were weighed and anesthetized with a ketamine:xylazine (2:1, v:v) mixture. A blood sample was collected by cardiac puncture. The animals were then sacrificed by asphyxiation with $CO_2$, the uterus was removed through a midline incision, and a wet uterine weight was determined.

A. Cholesterol Analysis

Blood samples were allowed to clot at room temperature for 2 hours, and serum was obtained following centrifugation for 10 minutes at 3000 rpm. Serum cholesterol was determined using a Boehringer Mannheim Diagnostics high performance cholesterol assay. Briefly the cholesterol was oxidized to cholest-4-en-3-one and hydrogen peroxide. The hydrogen peroxide was then reacted with phenol and 4-aminophenazone in the presence of peroxidase to produce a p-quinone imine dye, which was read spectrophotometrically at 500 nm. Cholesterol concentration was then calculated against a standard curve. The entire assay was automated using a Biomek Automated Workstation.

B. Uterine Eosinophil Peroxidase (EPO) Assay

Uteri were kept at 4° C. until time of enzymatic analysis. The uteri were then homogenized in 50 volumes of 50 mM Tris buffer (pH—8.0) containing 0.005% Triton X-100. Upon addition of 0.01% hydrogen peroxide and 10 mM o-phenylenediamine (final concentrations) in Tris buffer, increase in absorbance was monitored for one minute at 450 nm. The presence of eosinophils in the uterus, as measured by assay of eosinophil peroxidase activity, is an indication of estrogenic activity of a compound. The maximal velocity of a 15 second interval was determined over the initial, linear portion of the reaction curve.

C. Results

Data presented in Table 1 below show comparative results among control ovariectomized rats, rats treated with $EE_2$, and rats treated with certain compounds of the present invention. Although $EE_2$ caused a decrease in serum cholesterol when orally administered at 0.1 mg/Kg/day, it also exerted a marked stimulatory action on the uterus so that the uterine weight of $EE_2$ treated rats was substantially greater than the uterine weight of ovariectomized test animals. This uterine response to estrogen is well recognized in the art.

In contrast, the compounds of the present invention substantially reduce serum cholesterol compared to the ovariectomized control animals without the general increase of uterine weight that is associated with estrogen compounds known in the art. This benefit of serum cholesterol reduction without adversely affecting uterine weight is quite rare and desirable.

As is expressed in the data below, estrogenicity also was assessed by evaluating the adverse response of eosinophil infiltration into the uterus. The compounds of the present invention did not cause an increase in the number of eosinophils observed in the stromal layer of ovariectomized rats, or in rare instances an increase only at the highest concentrations tested, as measured by assay of eosinophil peroxidase activity, while $EE_2$ caused a substantial, expected increase in eosinophil infiltration.

The data presented in Table 1 reflect the response of 5 or 6 rats per treatment.

TABLE 1

| Example | Dose (mg/kg PO) | Uterine Weight (% inc. OVX) | Uterine EPO (Vmax) | Serum Cholesterol (% decrease OVX) |
|---|---|---|---|---|
| Ethynyl estradiol | 0.1 | 144.1* | 123.9* | 80.3* |
| 7 | 0.1 | 26.4 | 7.5 | -4.4 |
|  | 1 | 18.6 | 4.8 | 12.0 |
|  | 10 | 48.4* | 8.4 | 28.7* |
| 8 | 0.1 | 16.2 | 4.8 | -23.3 |
|  | 1 | 66.9* | 13.5 | 17.2 |
|  | 10 | 75.0* | 23.1 | 62.3* |
| 4 | 0.1 | 3.5 | 3.3 | -16.6 |
|  | 1 | 23.1 | 1.2 | 37.5* |
|  | 10 | 16.7 | 1.8 | 47.5* |
| 6 | 0.1 | 17.1 | 4.5 | 4.7 |
|  | 1 | 45.4* | 3.3 | 42.0* |
|  | 10 | 43.0* | 6.0 | 65.1* |
| 2 | 0.1 | -5.0 | 1.8 | -0.5 |
|  | 1 | 15.8 | 2.4 | 13.6 |
|  | 10 | 35.6* | 2.1 | 42.4* |

*Indicates value is significantly different than OVX control.

In addition to the demonstrated benefits of the compounds of the present invention, especially when compared to estradiol, the above data clearly demonstrate that these compounds are not estrogen mimetics. Furthermore, no deleterious toxicological effects (survival) were observed with treatment by any of the compounds of the present invention.

III. MCF-7 Proliferation Assay

MCF-7 breast adenocarcinoma cells (ATCC HTB 22) were maintained in MEM (minimal essential medium, phenol red-free, Sigma, St. Louis, Mo.) supplemented with 10% fetal bovine serum (FBS) (V/V), L-glutamine (2 mM), sodium pyruvate (1 mM), HEPES {(N-[2-hydroxyethyl] piperazine-N'-[2-ethanesulfonic acid]10 mM}, non-essential amino acids and bovine insulin (1 μg/ml) (maintenance medium). Ten days prior to assay, MCF-7 cells were switched to maintenance medium supplemented with 10% dextran coated charcoal stripped fetal bovine serum (DCC-FBS) assay medium) in place of 10% FBS to deplete internal stores of steroids. MCF-7 cells were removed from maintenance flasks using cell dissociation medium (Ca++/Mg++ free HBSS (phenol red-free) supplemented with 10 mM HEPES and 2 mM EDTA). Cells were washed twice with assay medium and adjusted to 80,000 cells/ml. Approximately 100 ml (8,000 cells) were added to flat-bottom microculture wells (Costar 3596) and incubated at 37° C. in a 5% $CO_2$ humidified incubator for 48 hours to allow for cell adherence and equilibration after transfer. Serial dilutions of drugs or DMSO as a diluent control were prepared in assay medium and 50 ml transferred to triplicate microcultures followed by 50 ml assay medium for a final volume of 200 ml. After an additional 48 hours at 37° C. in a 5% $CO_2$ humidified incubator, microcultures were pulsed with tritiated thymidine (1 uCi/well) for 4 hours. Cultures were terminated by freezing at −70° C. for 24 hours followed by thawing and harvesting of microcultures. Samples were counted by liquid scintillation. Results in Table 2 below show the $ED_{50}$ for certain compounds of the present invention.

TABLE 2

| Compound | Y | $R^1, R^2$ | $ED_{50}$ (nM) |
|---|---|---|---|
| 2 | NH | OH, OH | 2 |
| 4 | S | OH, OH | 0.9 |
| 6 | NMe | OH, OH | 10 |
| 7 | SO2 | OMe, OMe | 1000 |
| 8 | SO2 | OH, OH | 30 |

IV. MCF-7 Estrogen Receptor Binding Assay

Representative compounds of the present invention were tested in an estrogen receptor binding assay in which the test compounds were allowed to compete for binding with tritiated 17β-estradiol.

In the assay, serial dilutions of the test compound were mixed with 0.5 nM of $^3$H-17β-estradiol, along with 0.5 mg/mL of protein from MCF-7 lysates, to a total volume of 0.14 mL. Binding was allowed to take place for 18 hours at 5_C., followed by the addition of 0.07 mL of dextran/charcoal and centrifugation to remove non-bound radioligand. Aliquots of supernate containing bound radioligand were mixed with scintillant and counted. Relative binding affinity (RBA) was calculated as:

$$RBA = \frac{IC_{50} \, 17b\text{-estradiol}}{IC_{50} \, \text{test compound}}.$$

The data for representative compounds of the present invention are presented in Table 3.

TABLE 3

| Example | Y | $R^1, R^2$ | RBA* |
|---|---|---|---|
| 2 | NH | OH, OH | 0.26 |
| 4 | S | OH, OH | 0.15 |
| 6 | NMe | OH, OH | 0.19 |
| 7 | SO2 | OMe, OMe | <0.002 |
| 8 | SO2 | OH, OH | 0.084 |

*RBA = 1 for 17β-estradiol

Combination Therapy

The present invention also provides a method of alleviating post-menopausal syndrome in women which comprises the aforementioned method using compounds of the present invention and further comprises administering to a woman an effective amount of estrogen or progestin. These treatments are particularly useful for treating osteoporosis and lowering serum cholesterol because the patient will receive the benefits of each pharmaceutical agent while the compounds of the present invention would inhibit undesirable side-effects of estrogen and progestin. Activity of these combination treatments in any of the post-menopausal tests, vide supra, indicates that the combination treatments are useful for alleviating the symptoms of post-menopausal symptoms in women.

Various forms of estrogen and progestin are commercially available. Estrogen-based agents include, for example, ethe-nyl estrogen (0.01–0.03 mg/day), mestranol (0.05–0.15 mg/day), and conjugated estrogenic hormones such as Premarin® (Wyeth-Ayerst; 0.3–2.5 mg/day). Progestin-based agents include, for example, medroxyprogesterone such as Provera® (Upjohn; 2.5–10 mg/day), norethylnodrel (1.0–10.0 mg/day), and nonethindrone (0.5–2.0 mg/day). A preferred estrogen-based compound is Premarin, and norethylnodrel and norethindrone are preferred progestin-based agents.

The method of administration of each estrogen- and progestin-based agent is consistent with that which is known in the art. For the majority of the methods of the present invention, compounds of the present invention are administered continuously, from 1 to 3 times daily. However, cyclical therapy may especially be useful in the treatment of endometriosis or may be used acutely during painful attacks of the disease. In the case of restenosis, therapy may be limited to short (1–6 months) intervals following medical procedures such as angioplasty.

As used herein, the term "effective amount" means an amount of compound of the present invention which is capable of alleviating the symptoms of the various pathological conditions herein described. The specific dose of a compound administered according to this invention will, of course, be determined by the particular circumstances surrounding the case including, for example, the compound administered, the route of administration, the state of being of the patient, and the pathological condition being treated. A typical daily dose will contain a nontoxic dosage level of from about 5 mg to about 600 mg/day of a compound of the present invention. Preferred daily doses generally will be from about 15 mg to about 80 mg/day.

The compounds of this invention can be administered by a variety of routes including oral, rectal, transdermal, subucutaneus, intravenous, intramuscular, and intranasal. These compounds preferably are formulated prior to administration, the selection of which will be decided by the attending physician. Thus, another aspect of the present invention is a pharmaceutical composition comprising an effective amount of a compound of the current invention, optionally containing an effective amount of estrogen or progestin, and a pharmaceutically acceptable carrier, diluent, or excipient.

The total active ingredients in such formulations comprises from 0.1% to 99.9% by weight of the formulation. By "pharmaceutically acceptable" it is meant the carrier, diluent, excipients, and salt must be compatible with the other ingredients of the formulation, and not deleterious to the recipient thereof.

Pharmaceutical formulations of the present invention can be prepared by procedures known in the art using well known and readily available ingredients. For example, the compounds of the current invention, with or without an estrogen or progestin compound, can be formulated with common excipients, diluents, or carriers, and formed into tablets, capsules, suspensions, powders, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl-pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

The compounds also can be formulated as elixirs or solutions for convenient oral administration or as solutions appropriate for parenteral administration, for example, by intramuscular, subcutaneous or intravenous routes. Additionally, the compounds are well suited to formulation as sustained release dosage forms and the like. The formulations can be so constituted that they release the active ingredient only or preferably in a particular physiological location, possibly over a period of time. The coatings, envelopes, and protective matrices may be made, for example, from polymeric substances or waxes.

Compounds of the present invention, alone or in combination with a pharmaceutical agent of the present invention, generally will be administered in a convenient formulation. The following formulation examples only are illustrative and are not intended to limit the scope of the present invention.

FORMULATIONS

In the formulations which follow, "active ingredient" means a compound of formula I.

Formulation 1: Gelatin Capsules

Hard gelatin capsules are prepared using the following:

| Ingredient | Quantity (mg/capsule) |
| --- | --- |
| Active ingredient | 0.1–1000 |
| Starch, NF | 0–650 |
| Starch flowable powder | 0–650 |
| Silicone fluid 350 centistokes | 0–15 |

The formulation above may be changed in compliance with the reasonable variations provided.

A tablet formulation is prepared using the ingredients below:

Formulation 2: Tablets

| Ingredient | Quantity (mg/tablet) |
| --- | --- |
| Active ingredient | 2.5–1000 |
| Cellulose, microcrystalline | 200–650 |
| Silicon dioxide, fumed | 10–650 |
| Stearate acid | 5–15 |

The components are blended and compressed to form tablets.

Alternatively, tablets each containing 2.5–1000 mg of active ingredient are made up as follows:

Formulation 3: Tablets

| Ingredient | Quantity (mg/tablet) |
| --- | --- |
| Active ingredient | 25–1000 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.1–1000 mg of medicament per 5 ml dose are made as follows:

Formulation 4: Suspensions

| Ingredient | Quantity (mg/5 ml) |
| --- | --- |
| Active ingredient | 0.1–1000 mg |
| Sodium carboxymethyl cellulose | 50 mg |
| Syrup | 1.25 mg |
| Benzoic acid solution | 0.10 ml |
| Flavor | q.v. |
| Color | q.v. |
| Purified water to | 5 ml |

The medicament is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

An aerosol solution is prepared containing the following ingredients:

Formulation 5: Aerosol

| Ingredient | Quantity (% by weight) |
| --- | --- |
| Active ingredient | 0.25 |
| Ethanol | 25.75 |
| Propellant 22 (Chlorodifluoromethane) | 70.00 |

The active ingredient is mixed with ethanol and the mixture added to a portion of the propellant 22, cooled to 30° C., and transferred to a filling device. The required amount is then fed to a stainless steel container and diluted with the remaining propellant. The valve units are then fitted to the container.

Suppositories are prepared as follows:

Formulation 6: Suppositories

| Ingredient | Quantity (mg/suppository) |
| --- | --- |
| Active ingredient | 250 |
| Saturated fatty acid glycerides | 2,000 |

The active ingredient is passed through a No. 60 mesh U.S. sieve and suspended in the saturated fatty acid glycerides previously melted using the minimal necessary heat. The mixture is then poured into a suppository mold of nominal 2 g capacity and allowed to cool.

An intravenous formulation is prepared as follows:

Formulation 7: Intravenous Solution

| Ingredient | Quantity |
| --- | --- |
| Active ingredient | 50 mg |
| Isotonic saline | 1,000 ml |

The solution of the above ingredients is intravenously administered to a patient at a rate of about 1 ml per minute.

Formulation 8: Combination Capsule I

| Ingredient | Quantity (mg/capsule) |
| --- | --- |
| Active ingredient | 50 |
| Premarin | 1 |
| Avicel pH 101 | 50 |
| Starch 1500 | 117.50 |
| Silicon Oil | 2 |
| Tween 80 | 0.50 |
| Cab-O-Sil | 0.25 |

Formulation 9: Combination Capsule II

| Ingredient | Quantity (mg/capsule) |
| --- | --- |
| Active ingredient | 50 |
| Norethylnodrel | 5 |
| Avicel pH 101 | 82.50 |
| Starch 1500 | 90 |
| Silicon Oil | 2 |
| Tween 80 | 0.50 |

Formulation 10: Combination Tablet

| Ingredient | Quantity (mg/capsule) |
| --- | --- |
| Active ingredient | 50 |
| Premarin | 1 |
| Corn Starch NF | 50 |
| Povidone, K29-32 | 6 |
| Avicel pH 101 | 41.50 |
| Avicel pH 102 | 136.50 |
| Crospovidone XL10 | 2.50 |
| Magnesium Stearate | 0.50 |
| Cab-O-Sil | 0.50 |

We claim:
1. A compound having the formula:

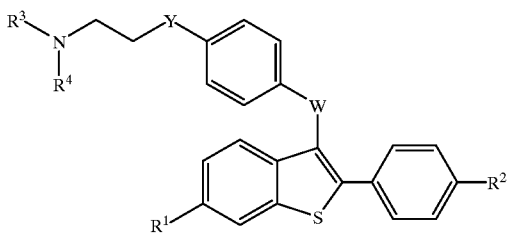

or a pharmaceutically acceptable salt thereof wherein
$R^1$ and $R^2$ are independently selected from the group consisting of hydrogen, halo, hydroxy, —O($C_1$–$C_6$ alkyl), —OC(O)($C_1$–$C_6$ alkyl), —OC(O)O($C_1$–$C_6$ alkyl), —OC(O)Ar, —OC(O)OAr, and —OSO$_2$($C_4$–$C_6$ alkyl);
where Ar is unsubstituted phenyl or is phenyl substituted with one or more substituents selected from the group consisting of alkyl of one to six carbon atoms, alkoxy of one to six carbon atoms, hydroxy, nitro, chloro, fluoro, trichloromethyl, and trifluoromethyl;
W is —CHOH—, —C(O)—, or —CH$_2$—;
Y is —CH$_2$—, —NH—, —NMe—, —S—, or —SO$_2$—; and
$R^3$ and $R^4$ are independently selected from the group consisting of H, alkyl of one to six carbon atoms, —C(O)($C_1$–$C_6$ alkyl), —C(O)NH($C_1$–$C_6$ alkyl), —C(O)Ar, where Ar is as defined above, or together with the nitrogen to which they are attached form 1-pyrrolidinyl, 1-piperidinyl, or a 5- or 6-membered imide or cyclic amide ring;
provided that when $R^3$ and $R^4$ are H, alkyl, or combine to form a 1-pyrrolidinyl, 1-piperidinyl, or a 5- or 6-membered imide ring, then $R^1$ and $R^2$ are independently selected from the group consisting of —OC(O)O($C_1$–$C_6$ alkyl), —OC(O)Ar', —OC(O)OAr, and —OSO$_2$($C_4$–$C_6$ alkyl); where Ar is as defined above and Ar' is phenyl substituted with one or more substituents selected from the group consisting of nitro, chloro, fluoro, trichloromethyl, and trifluoromethyl.

2. A compound as defined by claim 1 having the structure

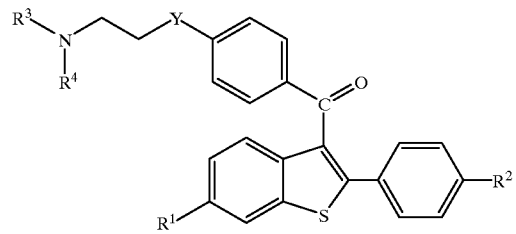

or a pharmaceutically acceptable salt thereof.

3. A compound as defined by claim 1 having the structure

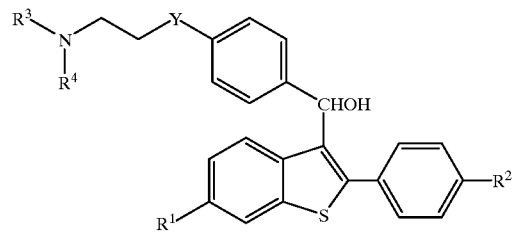

or a pharmaceutically acceptable salt thereof.

4. A compound as defined by claim 1 having the structure

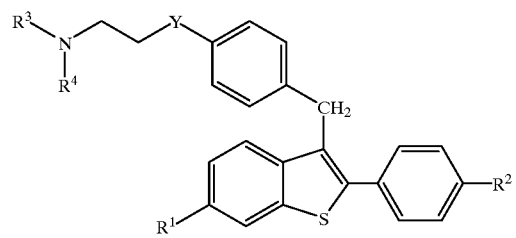

or a pharmaceutically acceptable salt thereof.

5. A compound as defined by claim 1 wherein $R^3$ and $R^4$ combine, together with the nitrogen atom to which they are attached, to form a 1-pyrrolidinyl or 1-piperidinyl ring, or a pharmaceutically acceptable salt thereof.

6. The compound of claim 1 wherein $R^1$ and $R^2$ are independently selected from —OH or —O($C_1$–$C_6$ alkyl) or a pharmaceutically acceptable salt thereof.

7. The compound of claim 6 wherein $R^1$ and $R^2$ are independently selected from —OH and —OCH$_3$.

8. The compound of claim 2 wherein Y is selected from the group consisting of —S—, —SO$_2$, —NH— and >NMe, or a pharmaceutically acceptable salt thereof.

9. An intermediate useful in the preparation of a compound according to claim 1 which is 6-methoxy-2-(4-methoxyphenyl)-3-(4-nitrobenzoyl)-benzo[b]thiophene.

10. A pharmaceutical composition comprising a therapeutically effective amount of compound as defined by claim 1 in combination with a pharmaceutically acceptable carrier, diluent, or excipient.

11. A method for treating osteoporosis comprising administering to a woman in need of such treatment a therapeutically effective amount of a compound of claim 1.

12. A method of treating hypercholesterolemia comprising administering to a woman in need of such treatment a therapeutically effective amount of a compound of claim 1.

13. A method of treating estrogen-dependent cancer comprising administering to a patient in need of such treatment a therapeutically effective amount of a compound of claim 1.

14. The method of claim 16 wherein said estrogen-dependent cancer is breast cancer.

15. A method for inhibiting aortal smooth muscle cell proliferation comprising administering to a patient in need of such treatment an effective amount of a compound of claim 1.

16. A method for inhibiting restenosis comprising administering to a patient in need of such treatment a therapeutically effective amount of a compound of claim 1.

\* \* \* \* \*